United States Patent [19]

Lammerts

[11] Patent Number: Plant 7,549

[45] Date of Patent: Jun. 11, 1991

[54] ROSE PLANT NAMED MARMALADE MIST

[75] Inventor: Walter Lammerts, Livermore, Calif.

[73] Assignee: DeVor Nurseries, Inc., Watsonville, Calif.

[21] Appl. No.: 495,900

[22] Filed: Mar. 19, 1990

[51] Int. Cl.[5] ..... A01H 5/00

[52] U.S. Cl. ..... Plt./20

[58] Field of Search ..... Plt./19-21

*Primary Examiner*—James R. Feyrer

*Attorney, Agent, or Firm*—Charles W. Rummler

[57] ABSTRACT

A new and distinct garden rose particularly distinguished by its continuous and profuse production of very large flowers having a generally delft rose coloration from early Spring to Winter blooming freely under natural conditions, the flowers being borne singly on strong stems of medium length from a vigorous, upright plant of medium height.

1 Drawing Sheet

BACKGROUND OF THE NEW PLANT

This new rose plant originated as a seedling of unknown parentage growing among a collection of rose plants maintained in my nursery at Watsonville, Calif. for breeding purposes. Because of the very large size of the blooms of this plant and their very pleasing coloration, I decided that this plant was an ideal subject for propagation and test for commercial purposes and propagation was done under my direction by budding at the DeVor nursery in Pleasanton, Calif. This was done through several generations at Pleasanton which demonstrated satisfactorily that the novel characteristics of this new plant would hold true from generation to generation and appeared to be firmly fixed.

This plant is now being reproduced on a commercial scale at the DeVor nursery at Orland, Calif.

DESCRIPTION OF THE DRAWING

My new rose plant is illustrated by the accompanying full color photographic drawing which shows a face view of a fully opened flower, the colors shown being as nearly true to those herein specified as is reasonably possible to obtain by conventional photographic procedures.

DESCRIPTION OF THE NEW VARIETY

The following is a detailed description of my new rose plant based upon observation of plants grown at Pleasanton, Calif., with the color designations specified herein being according to The R.H.S. Colour Chart published by The Royal Horticultural Society of London, England.

THE PLANT

Origin: Seedling.
Parentage: Unknown.
Classification:
- *Botanic.*—Grandiflora.
- *Commercial.*—Garden Rose.

Form: A tall, upright garden rose bush.
Height: About 100 to 110 cm, or about 7 feet.
Growth habit: Vigorous, upright and very sturdy.
Main stem:
- *Length.*—About 40 to 50 cm or about 1½ to 2 feet from last flower cut.
- *Color.*—Yellow green, 146-A.

- *Branching character.*—Free branching.

Foliage:
- *Quantity.*—Abundant.
- *Number of leaves.*—About 10 from the last flower cut.
- *Leaflets.*—Number: 3 to 5. Size: About 67 mm. long and about 48 mm. wide. Shape: Ovate with denticulate margin. Texture: Leathery. Aspect: Smooth and glossy. Color of Leaflets: Upper side — Yellow green 147-A. Under side — Yellow green 147-B.
- *Stipules.*—Adnate, slightly narrow.
- *Rachis.*—About 77 to 85 mm. on leaf having 5 leaflets; about 29 to 42 mm. on leaf having 3 leaflet.
- *Petioles.*—About 10 mm. on 3 leaflets and about 18 mm. on 5 leaflets.

Ribs and veins: Very slightly depressed on top.
Thorns:
- *Size.*—Varying in size, about 8 or 9 mm. long.
- *Color.*—Greyed purple 187-A on one side with greyed orange 165-A on the other side.

THE BUD

Size: Medium.
- *Diameter.*—About 28 mm.
- *Length.*—About 40 mm.

Shape: Tapering.
Rate of opening: Moderate.
Color of Petals:
- *When sepals first divide.*—Red 44-C.
- *When petals begin to unfurl.*—Red 42-C.

Sepals:
- *Number.*—Five.
- *Shape.*—Spreading with small leafs protruding.
- *Character.*—The sepals curl back when flowers open.
- *Color.*—Inside — Greyed Orange 176-A, covered with White 155-D with base color of Yellow Green 147-D. Outside — Greyed Purple 183-A with Yellow Green 144-A at the base.

Calyx:
- *Shape.*—Funnel margins at top and generously bulbous at the middle.
- *Width.*—About 14 mm.
- *Length.*—About 10 mm.
- *Size.*—Large.
- *Splitting.*—Calyx does not split.

*Aspect.*—Smooth.

Peduncle of flower stem:

*Length.*—About 73 to 84 mm.

*Character.*—Erect, sturdy and of medium size in length.

*Color.*—Greyed Orange 166-A.

THE FLOWER

Blooming habit: Continuous and profusely from early spring through mid-season and Fall blooming freely under natural conditions to late Fall.

Size of bloom: Very large.

*Diameter.*—About 133 mm.

*Depth.*—About 49 mm.

Borne: Singly on strong, upright stems.

Shape:

*When bloom first opens.*—High center.

*When bloom matures.*—The petals become nicely imbricated.

Petalage:

*Number.*—About 23.

*Number of florets.*—About 2.

*Arrangement.*—Imbricated.

*Form.*—Somewhat cupped with slightly lobed margins and fairly smooth apex.

*Texture.*—Soft-Leathery.

*Appearance.*—Velvety.

*Color.*—Outer petals — Delft Rose 47-C with base of Yellow 7-A. Reverse side — Red 48-B with base of 2-B. Inside petals — Red 48-B with base of Yellow 12-B. Reverse side — Red 48-C with base of Yellow 8-B.

Petaloids:

*Number.*—2.

*Size.*—About 35 mm.

*Color.*—Red 43-C with base of Yellow 13-A.

Flower stem:

*Length.*—About 72 to 80 mm.

*Color.*—Greyed Orange 166-A.

*Character.*—Sturdy and upright.

Fragrance: Slight fruity fragrance.

Persistence: Petals drop off.

Discoloration after full bloom: As flower matures, the colors progressively turn to Carmin Rose 52-D.

Disease resistance: Remarkably immune to mildew, rust, and black spot as observed at Watsonville, Calif.

Lasting quality: On the plant, medium and as cut flower, somewhat less.

THE REPRODUCTIVE ORGANS

Stamens:

*Number.*—About 150.

*Arrangement.*—Introrse.

*Anthers.*—Size: About 3 mm. Color: Yellow Orange 14-A around the lip with 14-C inside.

*Filaments.*—Length: About 9 to 12 mm. Color: Orange Red 31-C for inside threads, Yellow Orange 14-C for outside threads.

*Pollen.*—Color: Yellow Orange 14-A around lip and 14-C inside.

Pistils:

*Number.*—About 140.

*Styles.*—Length: About 12 mm. Color: Red 51-A at top with Yellow 2-D for rest of length.

*Stigmas.*—Color: Yellow Orange 16-C.

Character of the ovaries: Oblong with rounded edges and covered all over with silvery threads.

I claim:

1. A new and distinct variety of rose plant, substantially as herein shown and described, characterized by its profuse and continuous production of very large flowers of a generally Delft Rose color; and by its vigorous upright and free branching growth habit with abundant foliage as a garden rose plant.

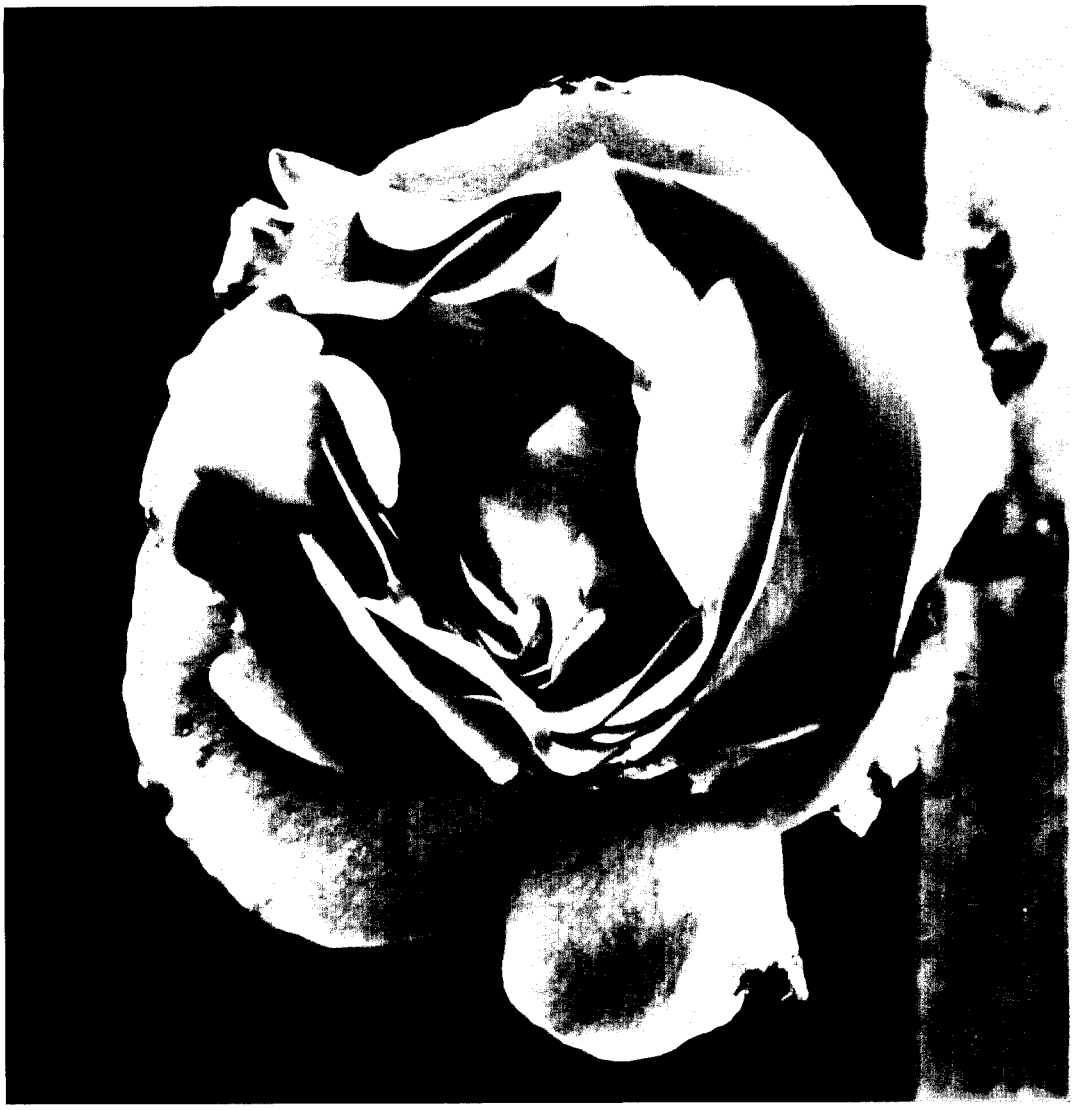

* * * * *